(12) United States Patent
Bandyopadhyay et al.

(10) Patent No.: US 11,998,369 B2
(45) Date of Patent: Jun. 4, 2024

(54) PACKAGING FOR MEDICAL DEVICES COATED WITH PERFLUORINATED LIQUIDS OR DISPERSIONS THEREOF

(71) Applicant: Freeflow Medical Devices LLC, Lancaster, PA (US)

(72) Inventors: Saibal Bandyopadhyay, Lancaster, PA (US); Andrew K. Jones, Lancaster, PA (US)

(73) Assignee: Freeflow Medical Devices LLC, Lancaster, PA (US)

( * ) Notice: Subject to any disclaimer, the term of this patent is extended or adjusted under 35 U.S.C. 154(b) by 285 days.

(21) Appl. No.: 17/228,474

(22) Filed: Apr. 12, 2021

(65) Prior Publication Data

US 2021/0369379 A1 Dec. 2, 2021

Related U.S. Application Data

(63) Continuation of application No. PCT/US2019/055743, filed on Oct. 10, 2019.

(60) Provisional application No. 62/744,223, filed on Oct. 11, 2018.

(51) Int. Cl.
*A61B 50/30* (2016.01)
*A61L 2/20* (2006.01)
*A61B 50/00* (2016.01)

(52) U.S. Cl.
CPC .............. *A61B 50/30* (2016.02); *A61L 2/206* (2013.01); *A61B 2050/005* (2016.02); *A61L 2202/181* (2013.01); *A61L 2202/24* (2013.01)

(58) Field of Classification Search
CPC ... A61B 50/30; A61B 2050/005; A61L 2/206; A61L 2202/181; A61L 2202/24

USPC .......................................................... 206/438
See application file for complete search history.

(56) References Cited

U.S. PATENT DOCUMENTS

| | | | |
|---|---|---|---|
| 3,068,187 A | 12/1962 | Bolstad et al. |
| 3,274,007 A | 9/1966 | Jones |
| 3,834,544 A | 9/1974 | Tyson, Jr. et al. |
| 3,927,981 A | 12/1975 | Viannay et al. |

(Continued)

FOREIGN PATENT DOCUMENTS

| | | |
|---|---|---|
| CN | 1360618 A | 7/2002 |
| CN | 1884398 A | 12/2006 |

(Continued)

OTHER PUBLICATIONS

Zhu et al., "Ice-phobic Coatings Based on Silicon-Oil-Infused Polydimethylsiloxane," American Chemical Society Applied Materials & Interfaces, vol. 5, pp. 4053-4062, (2013).

(Continued)

*Primary Examiner* — Steven A. Reynolds
(74) *Attorney, Agent, or Firm* — Meunier Carlin & Curfman LLC

(57) ABSTRACT

The present disclosure includes and provides for methods of packaging medical devices that are to be treated with a fluorinated liquid to alter their surface properties, packaging systems for such medical devices, and methods of utilizing the packaging systems to treat the medical devices. The packaging systems permit effective storage and distribution of medical devices that upon contact with mammalian blood have limited thrombogenicity or are non-thrombogenic and/ or are resistant to adhesion of blood cells or clots.

20 Claims, 3 Drawing Sheets

(56) References Cited

U.S. PATENT DOCUMENTS

| | | | |
|---|---|---|---|
| 4,386,170 A | 5/1983 | Monroe | |
| 4,633,004 A | 12/1986 | Boutvin et al. | |
| 4,787,991 A | 11/1988 | Morozumi et al. | |
| 4,861,511 A | 8/1989 | Kaplan | |
| 4,937,596 A | 6/1990 | Schmid | |
| 5,091,205 A | 2/1992 | Fan | |
| 5,178,267 A | 1/1993 | Grabenkort et al. | |
| 5,246,109 A * | 9/1993 | Markle | A61B 50/30 206/439 |
| 5,264,131 A | 11/1993 | Ishida et al. | |
| 5,277,176 A | 1/1994 | Habashi et al. | |
| 5,358,719 A | 10/1994 | Mellul et al. | |
| 5,372,888 A | 12/1994 | Ogawa et al. | |
| 5,425,989 A | 6/1995 | Ogawa et al. | |
| 5,429,184 A | 7/1995 | Bach et al. | |
| 5,578,340 A | 11/1996 | Ogawa | |
| 5,602,214 A | 2/1997 | Lin et al. | |
| 5,620,778 A | 4/1997 | Clatworthy | |
| 5,624,713 A | 4/1997 | Ramer | |
| 5,630,846 A | 5/1997 | Hara et al. | |
| 5,736,251 A | 4/1998 | Pinchuk | |
| 5,798,409 A | 8/1998 | Ho | |
| 5,804,318 A | 9/1998 | Pinchuk et al. | |
| 6,071,981 A | 6/2000 | Johnson et al. | |
| 6,171,673 B1 | 1/2001 | Tanaka et al. | |
| 6,232,379 B1 | 5/2001 | Takita | |
| 6,247,603 B1 | 6/2001 | Farrell et al. | |
| 6,447,919 B1 | 9/2002 | Brown et al. | |
| 6,511,753 B1 | 1/2003 | Teranishi et al. | |
| 6,830,149 B2 | 12/2004 | Merboth et al. | |
| 6,889,839 B1 * | 5/2005 | Rosten | B65D 81/075 206/583 |
| 7,189,934 B2 | 3/2007 | Youngner | |
| 7,192,993 B1 | 3/2007 | Sarangapani et al. | |
| 7,431,989 B2 | 10/2008 | Sakhrani et al. | |
| 7,560,492 B1 | 7/2009 | Claude et al. | |
| 7,666,514 B2 | 2/2010 | Sakamoto et al. | |
| 7,723,405 B2 | 5/2010 | Braun et al. | |
| 7,811,666 B2 | 10/2010 | Dry | |
| 7,877,968 B2 | 2/2011 | Kim et al. | |
| 9,121,306 B2 | 9/2015 | Aizenberg et al. | |
| 9,121,307 B2 | 9/2015 | Aizenberg et al. | |
| 9,265,578 B2 | 2/2016 | Dacey | |
| 9,353,646 B2 | 5/2016 | Aizenberg et al. | |
| 9,630,224 B2 | 4/2017 | Aizenberg et al. | |
| 9,932,484 B2 | 4/2018 | Aizenberg et al. | |
| 9,932,482 B2 | 5/2018 | Aizenberg et al. | |
| 10,011,800 B2 | 7/2018 | Aizenberg et al. | |
| 10,233,334 B2 | 3/2019 | Aizenberg et al. | |
| 10,550,272 B2 | 2/2020 | Aizenberg et al. | |
| 10,982,100 B2 | 4/2021 | Aizenberg et al. | |
| 11,118,067 B2 | 9/2021 | Aizenberg et al. | |
| 2001/0014711 A1 | 8/2001 | Levy | |
| 2003/0212232 A1 | 11/2003 | Majeti et al. | |
| 2004/0034941 A1 | 2/2004 | Iwato et al. | |
| 2004/0186211 A1 | 9/2004 | Howell et al. | |
| 2005/0003146 A1 | 1/2005 | Spath | |
| 2005/0164008 A1 | 7/2005 | Rukavina | |
| 2006/0024504 A1 | 2/2006 | Nelson et al. | |
| 2006/0153993 A1 | 7/2006 | Schmidt et al. | |
| 2006/0159645 A1 | 7/2006 | Miller et al. | |
| 2006/0194008 A1 | 8/2006 | Schwartz et al. | |
| 2006/0204645 A1 * | 9/2006 | Godfried | C23C 16/0245 427/2.1 |
| 2006/0211802 A1 | 9/2006 | Asgari | |
| 2007/0039832 A1 | 2/2007 | Heikenfeld | |
| 2007/0141306 A1 | 6/2007 | Kasai et al. | |
| 2007/0154626 A1 | 7/2007 | Sasaki et al. | |
| 2007/0166344 A1 | 7/2007 | Qu et al. | |
| 2007/0184733 A1 | 8/2007 | Manley et al. | |
| 2007/0224391 A1 | 9/2007 | Krupenkin et al. | |
| 2007/0254000 A1 | 11/2007 | Guo et al. | |
| 2008/0118763 A1 | 5/2008 | Balow et al. | |
| 2008/0195170 A1 | 8/2008 | Asgari | |
| 2009/0078153 A1 | 3/2009 | Shchukin et al. | |
| 2009/0098299 A1 | 4/2009 | Cheng | |
| 2009/0209922 A1 | 8/2009 | Boisjoly | |
| 2010/0009583 A1 | 1/2010 | Bringley et al. | |
| 2010/0021748 A1 | 1/2010 | Hu et al. | |
| 2010/0135852 A1 | 6/2010 | Kawakatsu et al. | |
| 2010/0145286 A1 | 6/2010 | Zhang | |
| 2010/0210745 A1 | 8/2010 | McDaniel et al. | |
| 2010/0285084 A1 | 11/2010 | Yang et al. | |
| 2011/0136653 A1 | 6/2011 | Koebel et al. | |
| 2011/0165206 A1 | 7/2011 | Liu et al. | |
| 2011/0203688 A1 | 8/2011 | Reed et al. | |
| 2011/0283778 A1 | 11/2011 | Angelescu et al. | |
| 2011/0287987 A1 | 11/2011 | Mordukhovich et al. | |
| 2011/0305881 A1 | 12/2011 | Schultz et al. | |
| 2012/0004357 A1 | 1/2012 | Roulleaux et al. | |
| 2012/0052241 A1 | 3/2012 | King et al. | |
| 2012/0141052 A1 | 6/2012 | Drew et al. | |
| 2012/0172787 A1 | 7/2012 | McClain et al. | |
| 2013/0032316 A1 | 2/2013 | Dhiman et al. | |
| 2013/0096545 A1 * | 4/2013 | Laudenslager | A61L 29/14 606/7 |
| 2013/0110222 A1 | 5/2013 | Slager | |
| 2014/0187666 A1 | 7/2014 | Aizenberg et al. | |
| 2014/0342954 A1 | 11/2014 | Ingber et al. | |
| 2015/0209198 A1 | 7/2015 | Aizenberg et al. | |
| 2015/0209846 A1 | 7/2015 | Aizenberg et al. | |
| 2015/0210951 A1 | 7/2015 | Aizenberg et al. | |
| 2016/0144079 A1 | 5/2016 | Ingber et al. | |
| 2016/0288062 A1 * | 10/2016 | Ait-Haddou | B01D 67/0095 |
| 2017/0367705 A1 | 12/2017 | Alston et al. | |
| 2018/0362875 A1 | 12/2018 | Aizenberg et al. | |
| 2021/0023292 A1 | 1/2021 | Bandyopadhyay et al. | |
| 2021/0369921 A1 | 12/2021 | Bandyopadhyay et al. | |

FOREIGN PATENT DOCUMENTS

| | | |
|---|---|---|
| CN | 101052667 A | 10/2007 |
| CN | 101198542 A | 6/2008 |
| CN | 101374607 A | 2/2009 |
| CN | 101444777 A | 6/2009 |
| CN | 101538395 A | 9/2009 |
| CN | 101580753 A | 11/2009 |
| CN | 101675156 A | 3/2010 |
| CN | 101918621 A | 12/2010 |
| CN | 102388180 A | 3/2012 |
| DE | 19818956 A1 | 11/1998 |
| EP | 0166998 A2 | 1/1986 |
| EP | 0338418 A1 | 10/1989 |
| EP | 0497204 A2 | 8/1992 |
| EP | 0893164 A2 | 1/1999 |
| EP | 1002825 A2 | 5/2000 |
| EP | 1487590 B1 | 5/2006 |
| EP | 2228053 A1 | 9/2010 |
| EP | 2363438 A1 | 9/2011 |
| FR | 2943066 A1 | 9/2010 |
| JP | S60-259269 A | 12/1985 |
| JP | 62-063219 A | 3/1987 |
| JP | S62-252477 A | 11/1987 |
| JP | 01-170932 A | 7/1989 |
| JP | 04-270649 A | 9/1992 |
| JP | 05-229402 A | 9/1993 |
| JP | 5240251 B2 | 9/1993 |
| JP | H06-180882 A | 6/1994 |
| JP | H06-48685 U | 7/1994 |
| JP | 07-242769 A | 9/1995 |
| JP | H08-12816 A | 1/1996 |
| JP | H10-183049 A | 7/1998 |
| JP | H11-64772 A | 3/1999 |
| JP | H11-345441 A | 12/1999 |
| JP | 2000-510353 A | 8/2000 |
| JP | 2001-131413 A | 5/2001 |
| JP | 2003-170540 A | 6/2003 |
| JP | 2004-037764 A | 2/2004 |
| JP | 2004-136630 A | 5/2004 |
| JP | 2005-082848 A | 3/2005 |
| JP | 2005-231084 A | 9/2005 |
| JP | 2006-280843 A | 10/2006 |
| JP | 2008-223003 A | 9/2008 |
| JP | 2009-523890 A | 6/2009 |

(56) References Cited

FOREIGN PATENT DOCUMENTS

| | | |
|---|---|---|
| JP | 2010-047890 A | 3/2010 |
| JP | 2010-167929 A | 8/2010 |
| JP | 6228012 B2 | 11/2017 |
| KR | 2009-0026199 A | 3/2009 |
| WO | 92/10532 A1 | 6/1992 |
| WO | 93/17077 A1 | 9/1993 |
| WO | 99/36490 A1 | 7/1999 |
| WO | 01/78800 A1 | 10/2001 |
| WO | 02/09647 A2 | 2/2002 |
| WO | 03/013827 A1 | 2/2003 |
| WO | 2005/091309 A1 | 9/2005 |
| WO | 2005/121288 A1 | 12/2005 |
| WO | 2006/091235 A1 | 8/2006 |
| WO | 2006/118460 A1 | 11/2006 |
| WO | 2007/130734 A2 | 11/2007 |
| WO | 2008/013825 A2 | 1/2008 |
| WO | 2008/017472 A1 | 2/2008 |
| WO | 2008/049108 A1 | 4/2008 |
| WO | 2008/120505 A1 | 10/2008 |
| WO | 2010/028752 A1 | 3/2010 |
| WO | 2010/042804 A2 | 4/2010 |
| WO | 2010/065960 A2 | 6/2010 |
| WO | 2010/116045 A1 | 10/2010 |
| WO | 2011/005200 A1 | 1/2011 |
| WO | 2011/049896 A2 | 4/2011 |
| WO | 2012009238 A2 | 1/2012 |
| WO | 2012/055821 A1 | 5/2012 |
| WO | 2012/055825 A1 | 5/2012 |
| WO | 2012/100099 A2 | 7/2012 |
| WO | 2012/100100 A2 | 7/2012 |
| WO | 2013/022467 A2 | 2/2013 |
| WO | 2013/106588 A1 | 7/2013 |
| WO | 2013/115868 A2 | 8/2013 |
| WO | 2014012039 A1 | 1/2014 |
| WO | 2014012052 A1 | 1/2014 |
| WO | 2014012072 A2 | 1/2014 |
| WO | 2014012078 A2 | 1/2014 |
| WO | 2014012079 A1 | 1/2014 |

OTHER PUBLICATIONS

Vogel et al., "Wafer-Scale Fabrication of Ordered Binary Colloidal Monolayers with Adjustable Stoichiometries," Advanced Functional Materials, vol. 21, pp. 3064-3073, (2011).
Voskerician et al., "Biocompatibility and biofouling of MEMS drug delivery devices," Biomaterials, vol. 24, pp. 1959-1967 (2003).
Wasserscheid et al., "Ionic Liquids in Synthesis," Wiley-VCH Verlag Gmbh & Co., 380 pages (2002).
Wenzel, "Resistance of Solid Surfaces to Wetting by Water", Industrial and Engineering Chemistry, 28(8):988-994, Aug. 1936, 7 pages.
Williams et al., "Etch Rates for Micromachining Processing—Part II," Journal of Microelectromechanical Systems, vol. 12, No. 6, pp. 761-778 (Dec. 2003).
Wilson et al., "Biosensors for real-time in vivo measurements," Biosens. Bioelectron, vol. 20, pp. 2388-2403 (Jan. 15, 2005).
Wong et al., "Deformation of DNA Molecules by Hydrodynamic Focusing," Journal of Fluid Mechanics, 2003, vol. 497, pp. 55-65.
Wong et al., "Bioinspired Self-Repairing Slippery Surfaces with Pressure-Stable Omniphobicity", Nature, 477(7365):443-447, Jan. 1, 2011.
Wong et al., "Closed-loop control of cellular functions using combinatory drugs guided by a stochastic search algorithm," Proceedings of National Academy of Science for the United States of America, vol. 105, No. 13, pp. 5105-5110 (Apr. 1, 2008).
Wool, "Self-Healing Materials: A Review", Soft Matter, 4:400-418, Advance Article published on line, Jan. 10, 2008.
Xu et al., "Approaching Zero: Using Fractured Crystals in Metrology for Replica Molding," J. Am. Chem. Soc., 2005, vol. 127, No. 3, pp. 854-855.

Zhao et al., "Antibacterial coatings on titanium implants," Journal of Biomedical Materials Research Part B: Applied Biomaterials, vol. 91, No. 1, pp. 4 70-480 (No Month Listed 2009).
Israelachvili, "Intermolecular and Surface Forces—Third Edition," Academic Press, 706 pages (No Month Listed 2011).
Karchmer et al., "*Staphylococcus epidermidis* causing prosthetic valve endocarditis: microbiologic and clinical observations as guides to therapy," Ann Intern Med, vol. 98, pp. 447-455 (Apr. 1, 1983).
Keck et al., "Preparation of partially fluorinated aryl/alkyl vinylene ether polymers," Polymer International, vol. 62, Issue 10, pp. 1485-1491, Oct. 2013.
Khoo et al., "Directed assembly of PEGylated-peptide coatings for infection-resistant titanium metal," J. Am. Chem. Soc., vol. 131, pp. 10992-10997 (Jul. 21, 2009).
Kim et al., "Structural Transformation by Electrodeposition on Patterned Substrates (STEPS): A new Versatile Nano-fabrication Method," Nano Letters, vol. 12, No. 2, pp. A-G (Mar. 2011).
Kobayashi et al., "Surface tension of poly[(3,3,4,4,5,5,6,6,6-nanoflurohexyl methlisiloxane]," Macromolecules, 1990, vol. 23, No. 23, pp. 4929-4933.
Koschwanez et al., "In vitro and in vivo characterization of porous poly-L-lactic acid coatings for subcutaneously implanted glucose sensors," Journal of Biomedical Materials Research Part A, pp. 792-807 (Dec. 2008).
Lee et al., "Fast fabrication of long-range ordered porous alumina membranes by hard anodization," Nature Mater, vol. 5, pp. 741-747 (Sep. 2006).
Leslie et al., "New anticoagulant coatings and hemostasis assessment tools to avoid complications withpediatric left ventricular assist devices," The Journal of Thoracic and Cardiovascular Surgery, vol. 154, pp. 1364-1366 (May 16, 2017).
Li et al., "Bioinspired Self-Healing Superhydrophobic Coatings," Angewandte Chemie, vol. 49, No. 35, pp. 6129-6133 (Aug. 16, 2010).
Lillehoj et al., "A self-pumping lab-on-a-chip for rapid detection of botulinium toxin," Lab Chips, vol. 10, pp. 2265-2270 (Jun. 11, 2010).
Lin et al., "Surface modification of polytetrafluoroethylene films by plasma pretreatment and graft copolymierization to improve their adhesion to bismaleimide," Polym. Int., vol. 58, No. 1, pp. 46-53 (Jan. 2009).
Liu et al., "Organogel-based Thin Films for Self-Cleaning on Various Surfaces," Advanced Materials, 5 pages, (2013).
Matsunaga, et al., "Controlling the Stability and Reversibility of Micropillar Assembly by Surface Chemistry," J. Am. Chem. Soc., vol. 133, No. 14, pp. 5545-5553, 4 pages (Dec. 2, 2011).
Meuler et al., "Relationships between Water Wettability and Ice Adhesion," ACS Applied Materials and Interfaces, vol. 2, No. 11, 31 pages (Oct. 15, 2010).
Microsurfaces, Inc., "Anti-Stiction Coatings in MEMS Devices," MicroSurfaces, Inc., retrieved from website URL: http://memsurface.com/stiction.html, 2 pages (retrieved on Dec. 8, 2011).
Miller-Chou et al., "A review of polymer dissolution," Progress in Polymer Science, vol. 28, pp. 1223-1270, (2003).
Mori, "Silicone Surface Treatment," Journal of the Society of Rubber Industry of Japan (Nippon Gomu Kyokaishi), 1986, vol. 59, Issue 11, pp. 627-633. ISSN: 0029-022X. Released Jul. 9, 2007. Full English translation with original. (<https://www.jstage.jst.go.jp/article/gomu1944/59/11/59 11 627/ article/-char/en>).
Munro et al., "Deterioration of pH electrode response due to biofilm formation on the glass membrane," Sensor Actuat B—Chem, vol. 37, pp. 187-194 (Dec. 1996).
Nakao, "Silicone Water Repellents," Journal of Synthetic Organic Chemistry, Japan, Jul. 1966, vol. 24, No. 7, pp. 598-608. Full English translation with original. ISSN 0037-9980. (<https://www.istaae.ist.ao.io/article/vukiaoseikvokaishi 1943/24/7 /24 7 598/ article/-char/en>).
Nguyen, "Quantitative Testing of Robustness on Superomniphobic Surfaces by Drop Impact", Langmuir, 26(23):18369-18373, Dec. 7, 2010.
Niimi et al., "The effects of heparin coating of oxygenator fibers on platelet adhesion and protein adsorption," Anesth. Analg., 1999, vol. 89, pp. 573-579.

(56) References Cited

OTHER PUBLICATIONS

Noetzel et al., "Shunt fluid examination: risks and benefits in the evaluation of shunt malfunction and infection," J. Neurosurg., vol. 61, pp. 328-332 (Aug. 1984).
Nosonovsky et al., "Biomimetic Superhydrophobic Surfaces: Multiscale Approach", Nano Lett, 7(9):2633-2637, Aug. 17, 2007.
Nosonovsky, "Multiscale Roughness and Stability of Superhydrophobic Biomimetic Interfaces", Lanamuir, 23(6):3157-3161, Feb. 13, 2007.
O'Toole et al., "Biofilm Formation as Microbial Development," Annu. Rev. Microbiol., 2000, vol. 54, pp. 49-79.
Park et al., "Bacterial adhesion on PEG modified polyurethane surfaces," Biomaterials, vol. 19, No. 7-9, pp. 851-859 (Apr.-May 1998).
Poetes et al., "Metastable Underwater Superhydrophobicity," Physical Review Letters, vol. 105, Issue 16, pp. 166104.1-166104.4 Published (Oct. 14, 2010).
Pokroy et al., "Fabrication of Bio-Inspired Actuated Nanostructures with Arbitrary Geometry and Stiffness," Adv. Mater, vol. 21, pp. 463-469 (Jan. 26, 2009).
Prakash et al., "Microfluidic Bubble Logic," Science, vol. 315, No. 5813, pp. 832-835 (Sep. 2008).
Prime et al., "Self-assembled organic monolayers: model systems for studying adsorption of proteins at surfaces," Science, vol. 252, No. 5009, pp. 1164-1167 (May 24, 1991).
Quere, "Wetting and roughness," Annu. Rev. Mater. Res., vol. 38, pp. 71-99 (Apr. 7, 2008).
Raza et al., "Superhydrophobic Surfaces by Anomalous Fluoroalkylsilane Self-Assembly on Silica Nanosphere Arrays", Langmuir, 26(15):12962-12972, Aug. 3, 2010.
Vogel et al., "From soft to hard: the generation of functional and complex colloidal monolayers for nanolithography," Soft Matter, vol. 8, pp. 4044-4061 (2012).
Rothemund, "Folding DNA to create nanoscale shapes and patterns," Nature, vol. 440, pp. 297-302, Mar. 16, 2006.
Rowe, "Chemistry and Technology of Flavors and Fragrances," Blackwell Publishing Ltd, 12 pages—Title Page, Copyright Page and Table of Contents Only (2005).
Saido et al., "A Growth of Aspergillus Niger on Surface of Polymer Films was Observed by FT-IR and Scanning Electron Microscope", Materials Life, Oct. 8, 1991, vol. 3 No. 4, pp. 218-224. English translation.
Shaffer et al., "Liquid Ventilation," Pediatric Pulmonology, vol. 14, pp. 102-109 (Oct. 1992).
Tuteja et al., "Designing Superoleophobic Surfaces," Science, vol. 318, No. 5856, pp. 1618-1622 (Dec. 7, 2007).
Shafrin et al., "Constitutive relations in the wetting of low energy surfaces and the theory of the retraction method of preparing monolayers," J. Phys. Chem., vol. 64, pp. 519-524 (May 1960).
Shi et al., "Microstructure and friction properties of PVA/PVP hydrogels for articular cartilage repair as function of polymerization degree and polymer concentration," Wear, Jul. 30, 2013, vol. 305, pp. 280-285.
Skattum et al., "Complement deficiency states and associated infections," Mol. Immunol, vol. 48, No. 14, pp. 1643-1655 (Aug. 2011).
Sohail et al., "Risk factor analysis of permanent pacemaker infection," Clin Infect Dis, vol. 45, pp. 166-173 (Jul. 15, 2007).
Stober et al., "Controlled growth of monodisperse silica spheres in the micron size range," Journal of Colloid and Interface Science, vol. 26, No. 1, pp. 62-69 (Jan. 1968).
Trevors, "Silver resistance and accumulation in bacteria," Enzyme and Mircobial Technology, vol. 9, No. 6, pp. 331-333 (Jun. 1987).
Tuli et al., "Risk factors for repeated cerebrospinal shunt failures in pediatric patients with hydrocephalus," J. Neurosurg., vol. 92, pp. 31-38 (Jan. 2000).
Tuteja et al., "Robust omniphobic surfaces," PNAS, vol. 105, No. 47, pp. 18200-18205 (Nov. 25, 2008).
Varanasi et al., "Frost formation and ice adhesion on superhydrophobic surfaces," Applied Physics Letters, 2010, vol. 97, pp. 234102-1-234102-3.
Vogel et al., "A Convenient Method to Produce Close- and Non-close-Packed Monolayers using Direct Assembly at the Air-Water Interface and Subsequent Plasma-Induced Size Reduction," Macromolecular Chemistry and Physics, vol. 212, pp. 1719-1734 (2011).
International Search Report and Written Opinion, International Application No. PCT/US2019/055743 (published under WO 2020/077161), 14 pages (dated Dec. 13, 2019).
Abbott et al., "Mass Production of Bio-Inspired Structured Surfaces", Proceedings of the Institution of Mechanical Engineers, Part C: Journal of Mechanical Engineering Science, 221(10):1181-1191, Oct. 1, 2007.
Afessa et al., "Association Between a Silver-Coated Endotracheal Tube and Reduced Mortality in Patients With Ventilator-Associated Pneumonia," Chest, vol. 137, pp. 1015-1021 (May 2010).
Ahuja et al., "Nanonails: A Simple Geometrical Approach to Electrically Tunable Superlyophobic Surfaces," Langmuir, 2008, vol. 24, pp. 9-14.
Akamatsu, "Water-repellent Coating on Glass," New Glass, Sep. 2006, vol. 21, No. 3, pp. 27-34. Full English translation with original. ISSN 0914-6563. (<https://www.newglass.jp/mag/TITL/maghtml/82e.html>).
Badrossamay et al., "Nanofiber Assembly by Rotary Jet-Spinning," Nano Letters, vol. 10, No. 6, pp. 2257-2261, 11 pages (Jun. 9, 2010).
Bai et al., "Core-Annular Flows," Annual Review Fluid Mechanics, vol. 29, pp. 65-90 (Jan. 1997).
Banerjee et al., "Antifouling coatings: recent developments in the design of surfaces that prevent fouling by proteins, bacteria, and marine organisms," Advanced Materials, 2011, 23, pp. 690-718.
Banerjee et al., "Infection control during GI endoscopy," Gastrointest Endosc, vol. 67, pp. 781-790 (May 2008).
Banhart, "Manufacture, characterisation and application of cellular metals and metal forms," Progress in Materials Science, 2001, vol. 46, pp. 559-632.
Barstad et al., "Monocyte procoagulant activity induced by adherence to an artificial surface is reduced by end-point immobilized heparin-coating of the surface", Thrombosis and haemostatis, 1997, vol. 79, pp. 302-305.
Barthlott et al., "Purity of the sacred lotus, or escape from contamination in biological surfaces," Planta, 1997, vol. 202, pp. 1-8.
Bauer et al., "The Insect-Trapping Rim of Nepenthes Pitchers", Plant Signaling & Behavior, 4(11):1019-1023, Nov. 1, 2009.
Beely et al., "Electron Microscopy as a Tool for Assessment of Anticoagulation Strategies During Extracorporeal Life Support: The Proof Is on the Membrane," ASAIO Journal, vol. 62(5), pp. 525-532 (Oct. 2016).
Beilenhoff et al., "ESGE-ESGENA guideline: Cleaning and disinfection in gastrointestinal endoscopy Update 2008," Endoscopy, 2008, vol. 40, pp. 939-957.
Berger, R. G., "Flavours and Fragrances: Chemistry, Bioprocessing and Sustainability," Springer, 15 pages—Title Page, Copyright Page and Table of Contents Only (Feb. 14, 2007).
Bhardwaj et al., "A review of the development of a vehicle for localized and controlled drug delivery for implantable biosensors," J. Diabetes Sci Technol., vol. 2, pp. 1016-1029 (Nov. 2008).
Bico et al., "Rough wetting," Europhysics Letters, vol. 55, No. 2, pp. 214-220 (Jul. 15, 2001).
Bico et al., "Wetting of textured surfaces," Colloids and Surfaces, A: Physicochemical and Engineering Aspects, 2002, vol. 206, pp. 41-46.
Bocquet et al., "A smooth future?," Nature Mater, vol. 10, pp. 334-337 (May 2011).
Bohn et al., "Insect Aquaplaning: Nepenthes Pitcher Plants Capture Prey with the Peristome, a Fully Wettable Water-Lubricated Anisotropic Surface", PNAS, 101 (39):14138-14143, Sep. 21, 2008.
Bos et al., "Retention of bacteria on a substratum surface with micro patterned hydrophobicity," Fems Microbiology Letters, vol. 189, No. 2, pp. 311-315 (Aug. 15, 2000).
Cassie et al., "Wettability of Porous Surfaces", Transactions of the Faraday Society, 1944, vol. 40, pp. 546-551.
Cassie et al., "Large contact angles of plant and animal surfaces," Nature, vol. 155, pp. 21-22, Jan. 6, 1945.

(56) References Cited

OTHER PUBLICATIONS

Chaudhury et al., "Direct Measurement of Interfacial Interactions between Semispherical Lenses and Flat Sheets of Poly (dimethysiloxane) and Their Chemical Derivatives," Langmuir, 1991, vol. 7, pp. 1013-1025.
Chen et al., "Surface hydration: Principles and applications toward low-fouling/nonfouling biomaterials," Polymer, vol. 51, pp. 5283-5293 (Aug. 10, 2010).
Clark, Jr. et al., "Survival of Mammals Breathing Organic Liquid Equilibriated With Oxygen at Atmospheric Pressure", Science, vol. 152, pp. 1755-1756 (Jun. 24, 1966).
Costerton et al., "Bacterial biofilms in nature and disease," Ann. Rev. Microbiol, 1987, vol. 41, pp. 435-464.
Costerton et al., "Bacterial biofilms: a common cause of persistent infections," Science, vol. 284, No. 5418, pp. 1318-1322 (May 21, 1999).
Cribier et al., "Percutaneous transcatheter implantation of an aortic valve prothesis for calcific aortic stenosis—First human case description," Circulation, vol. 106, pp. 3006-3008 (Nov. 25, 2002).
Crnich et al., "The Promise of Novel Technology for the Prevention of Intravascular Device-Related Bloodstream Infection. I. Pathogenesis and Short-Term Devices," Clinical Infectious Diseases, vol. 34, pp. 1232-1242 (May 1, 2002).
Database WPI Weekly 198933, Thomson Scientific, London, GB, XP-002694116; AN 1989-237086 & JP1170932A (Nippon Sheet Glass Co. Ltd.) 1 page (Jul. 6, 1989) (abstract).
De Beer et al., "Microbial Biofilms," Prokaryotes, 2006, vol. 1, pp. 904-937.
De Gennes et al., "Capillarity and Wetting Phenomena: drops, bubbles, pearls, waves," Springer, New York, 2004.
Dieter, "Coronary artery stent infection," Clin. Cardiol., vol. 23, pp. 808-810 (Jan. 6, 2000).
Dismukes et al., "Prosthetic valve endocarditis. Analysis of 38 cases," Circulation, vol. 48, pp. 365-377 (Aug. 1973).
Drelich et al., "Measurement of Interfacial Tension in Fluid-Fluid Systems", Encyclopedia of Surface and Colloid Science, pp. 3152-3166 (Jan. 2002).
Fadeev et al., "Surface Modification of Poly(ethylene terephthalate) To Prepare Surfaces with Silica-Like Reactivity," Langmuir, vol. 14, No. 19, pp. 5586-5593 (Aug. 21, 1998).
Fowkes, "Attractive forces at interfaces," Ind. Eng. Chem., vol. 56, pp. 40-52 (Dec. 1964).
Fuerstman, et al., "Coding/Decoding and Reversibility of droplet trains in Microfluidic networks," Science, vol. 315, No. 5813, pp. 828-832 (Feb. 9, 2007).
Gao et al., "Teflon is Hydrophobic Comments on Definitions of Hydrophobic, Shear versus Tensile Hydrophobicity, and Wettability Characterization," Langmuir, vol. 24, pp. 9183-9188 (Sep. 2, 2008).
Garg et al., "Acute Coronary Syndrome Caused by Coronary Artery Mycotic Aneurysm Due to Late Stent Infection Localized With Radiolabeled Autologous Leukocyte Imaging," Clin. Nucl. Med., vol. 34, pp. 753-755 (Nov. 2009).
George et al., Self-assembling polystyrene-block poly(ethylene oxide) copolymer surface coatings: resistance to protein and cell adhesion, Biomaterials, vol. 30 pp. 2449-2456 (May 2009).
Gristina et al., "Biomaterial-centered sepsis and the total artifical heart. Microbial adhesion vs tissue inteqration," JAMA, vol. 259, pp. 870-874 (Feb. 1988).
Hall-Stoodley et al., "Bacterial biofilms: from the natural environment to infectious diseases," Nature Reviews Microbiology, vol. 2, No. 2, pp. 95-108 (Feb. 2004).
Hatton et al., "Assembly of large-area, highly ordered, crack-free inverse opal films," Proceedings of the National Academy of Science of the United States of America, vol. 107, No. 23, pp. 10354-10359 (Jun. 8, 2010).
Hearn et al., "Endovascular stent infection with delayed bacterial challenge," American Journal of Surgery, vol. 174, pp. 157-159 (Aug. 1997).
Hejazi et al., "Wetting Transitions in Two-, Three-, and Four-Phase Systems", Langmuir, 2B:2173-2180, Nov. 5, 2011.
Hozumi et al., "Hydrophobization of Metal/Metal Oxide Surfaces Using Monolayer Films", Journal of the Surface Finishing Society of Japan, Oct. 9, 2009, vol. 60, No. 1, pp. 16-20. English translation.
Inazaki et al., "Surface modification of poly (tetrafluoroethylene) with ArF excimer laser irradiation," J. Photopoly. Sci. Technol. vol. 7, No. 2, pp. 389-395 (1994).
Ishino et al., "Wicking Within Forests of Micropillars", EPL Journal, vol. 79, pp. 56005-p1-56005-p5, Sep. 2007.
International Search Report and Written Opinion dated Jan. 3, 2020, for International Application No. PCT/US2019/055742.
International Search Report and Written Opinion dated May 14, 2019, for International Application No. PCT/US2019/012580.
Lafuma A et al. Slippery pre-suffused surfaces; Europhysics Letters: A Letters Journal Exploring the Frontiers of Physics, Institute of Physics, vol. 96, No. 5, Nov. 3, 2011.
International Search Report and Written Opinion dated Aug. 21, 2012 for PCT/US2012/021929.
International Search Report and Written Opinion dated Jun. 6, 2013, for PCT/US2013/021056.
International Search Report and Written Opinion dated Dec. 4, 2013, for PCT/US2013/050403.
International Search Report and Written Opinion dated Sep. 5, 2013, for PCT/US2013/050364.
International Search Report and Written Opinion dated May 13, 2014, for PCT/US2013/050396.
International Search Report and Written Opinion dated Jun. 4, 2014, for PCT/US2013/050402.
International Search Report and Written Opinion dated Sep. 13, 2013, for PCT/US2013/050343.
International Search Report and Written Opinion dated Aug. 10, 2012, for PCT/US2012/021928.

\* cited by examiner

PACKAGING FOR MEDICAL DEVICES COATED WITH PERFLUORINATED LIQUIDS OR DISPERSIONS THEREOF

RELATED APPLICATIONS

This application is a continuation of International Application No. PCT/US2019/055743 filed Oct. 10, 2019, which claims the benefit of U.S. Provisional Application No. 62/744,223 filed Oct. 11, 2018, each of which applications is incorporated herein by reference in its entirety.

BACKGROUND

Medical devices, or components of medical devices, may comprise fluoropolymers and/or perfluoropolymers, may be coated with a layer of fluoropolymers and/or perfluoropolymers, or may be coated with fluorinated organic groups (e.g., fluorinated alkane groups such as those that may be appended to a surface by the reaction of a fluoroalkyl silane with the device). Advanced coatings on such medical devices may employ fluorinated and/or perfluorinated liquids that associate with the fluoropolymers and/or perfluoropolymers or fluorinated organic groups and prevent the initiation of thrombi, cell adhesion, and/or biofilm formation on the surface when exposed to mammalian tissue, cerebrospinal fluid, blood etc. ex vivo or is implanted or inserted into a mammalian (e.g., human) body. A fundamental challenge of packaging those types of advanced coatings is sterilization. It is difficult to employ a single method to sterilize both the device and the liquid on the device as the sterilization processes can cause degradation of the device and/or fluorinated liquids or loss of the fluorinated liquids. A preferred method of sterilizing medical equipment, ethylene oxide sterilization, uses heat that will evaporate and remove some or all of the fluorinated liquid(s) on the device. The present disclosure provides a method of sterilizing the perfluorinated liquid separately from the device itself.

SUMMARY

The present disclosure includes and provides for methods of packaging medical devices that are to be treated with a fluorinated liquid to alter their surface properties, packaging systems for such medical devices, and methods of utilizing the packaging systems to treat the medical devices. The packaging systems provided herein permit effective storage and distribution of medical devices that upon contact with mammalian blood (e.g., human blood) have limited thrombogenicity or are non-thrombogenic (resistant to clot formation) and/or are resistant to adhesion of blood cells or clots. The treated devices are also resistant to the adhesion of biological organisms and/or the growth and/or adhesion of biofilms on the surface treated with the fluorinated liquid (e.g., fluorocarbon, perfluorocarbon, or fluoroalkyl containing molecules).

In an embodiment the disclosure includes and provides for a medical device packaging system comprising: (i) a base having a channel conforming to the shape of a medical device; (ii) a cover forming a substantially gas and liquid tight seal over the channel (thereby closing the channel from the external environment), wherein the cover can be peeled away from the base exposing all or part of the channel (or the cover can be slit or perforated if desired); and (iii) a medical device disposed in the channel (the medical device optionally comprising a fluoropolymer and/or perfluoropolymer component or coating on all or part of its surface); wherein the medical device optionally comprises a connector to the medical device that is also disposed in the channel. The packaging system may further comprise a fluorinated liquid.

The packaging systems described herein permit final preparation of devices treated with a fluorinated liquid (e.g., a fluorocarbon or perfluorcarbon liquid) at the point of care where the treated medical devices are employed. Embodiments that comprise packaging the fluorinated liquids in reservoirs separate from the medical device avoid long term storage of devices with the potential for loss of the fluorinated liquids by, for example, diffusion through the packaging materials. Moreover, packaging the medical devices, including those with fluoropolymer or perfluoropolymer components, in packaging with a cover that is permeable to ethylene oxide permits sterilization without the potential damage to the device and release of hydrofluoric acid (HF) that can be caused by radiation sterilization.

DEFINITIONS

As used herein, fluorinated with respect to a molecule means molecules having fluorine in place of hydrogen. Fluorinated molecules include perfluorinated molecules where all hydrogens have been substituted with a fluorine.

"Fluorinated liquids" as used herein refer to chemical compositions that are liquid at 22° C. and one atmosphere of pressure comprised of, consisting essentially of, or consisting of hydrocarbons, or molecules having a hydrocarbon moiety (e.g., an alkyl group), in which one or more hydrogen atoms bound to a carbon atom have been replaced by a fluorine atom. Fluorinated liquids include perfluorinated liquids where each hydrogen atom has been replaced by a fluorine atom. The term "fluorinated liquid" is understood to include compositions comprising one or more fluorinated liquids and/or perfluorinated liquids unless stated otherwise.

"Gas and liquid tight seal" means that bulk gas or liquid cannot pass through the seal/sealing material; however, gases, depending on their nature and the physical conditions (temperature, pressure etc.) may pass through the sealing material. For example, sterilizing gases, such as ethylene oxide, may pass through the seal or sealing material by processes such as diffusion.

DETAILED DESCRIPTION

I. Medical Device Packaging Systems

Figure 1:
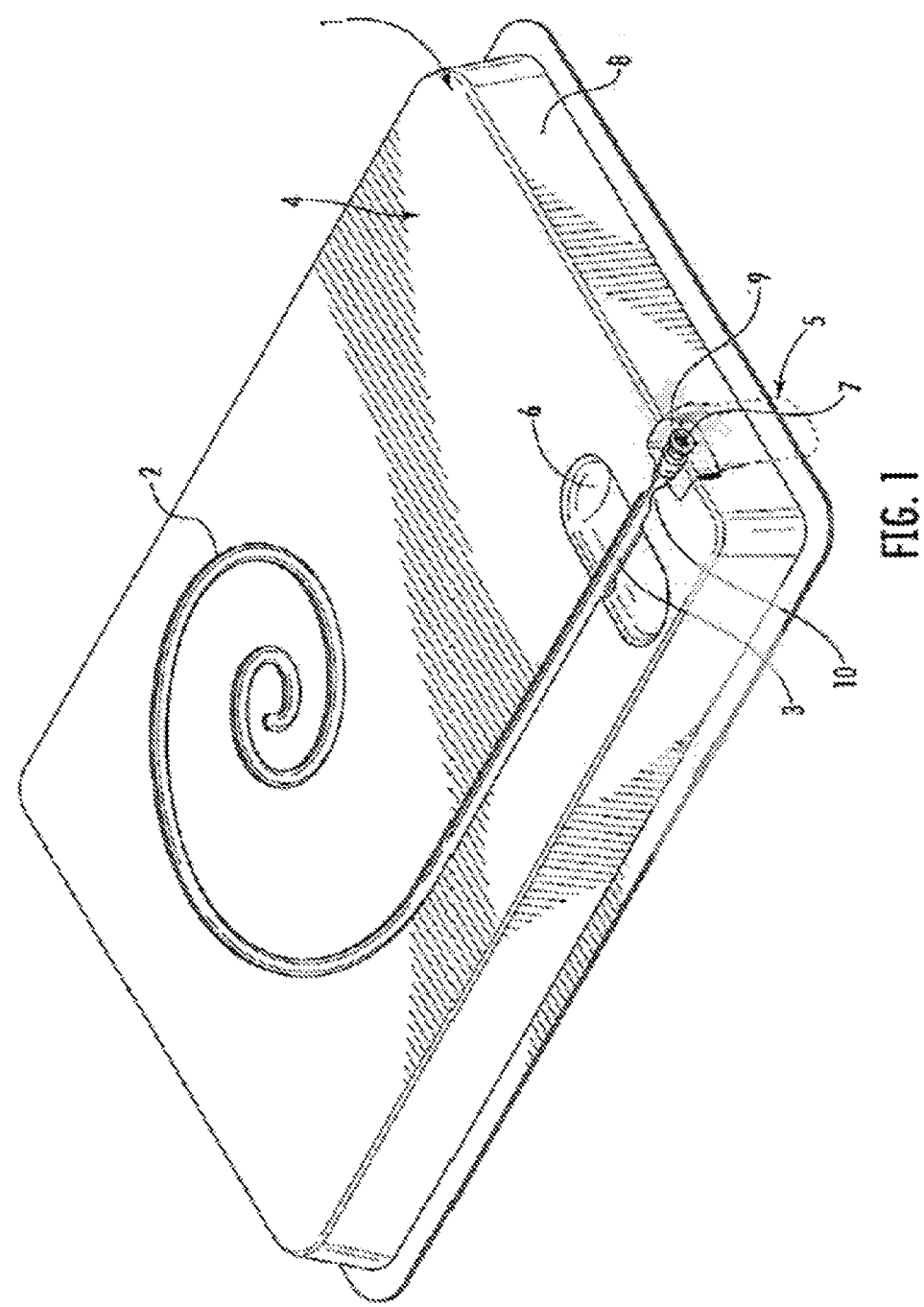
FIG. 1 shows an embodiment of a medical device packaging system having a base 1 with a channel 2 in which a medical device 3 is disposed. The base has a substantially planar surface on which a cover 4 is located. The cover has a section extending over and covering the expanded and/or exposed end of the channel 9 where it meets the side 8 of the base. Also shown is an optional constricted section 10 of the channel that engages the medical device and/or the optional connector 7 attached to the end of the medical device. In addition, the cover may have an optional tab 5 to aid in its removal and an optional expanded region of the channel (or a depression) 6 permitting the medical device to be grasped with fingers or forceps.

The present disclosure includes and provides for medical device packaging systems comprising:
  (i) a base 1 having a channel 2 substantially conforming to the shape of a medical device 3;
  (ii) a cover 4 forming a substantially gas and liquid tight seal over the channel (thereby closing the channel from the external environment and maintaining a sterile environment in the channel once formed), wherein the cover can be removed or opened (e.g., peeled away from the base using e.g., tab 5), exposing all or part of the channel (the cover can also be slit or perforated, such as with a knife, if desired); and
  (iii) a medical device disposed in the channel (the medical device optionally comprising a fluoropolymer and/or perfluoropolymer component or coating on all or part of its surface);
wherein the channel optionally has an expanded region 6 permitting the device to be grasped by human fingers or forceps; and
wherein the medical device optionally comprises a connector 7 that is also disposed in whole or in part in the channel. See, e.g., the embodiment shown in FIG. 1.

The channel within the base and its cover serve to hold and position the medical device within the base, protecting it and maintaining the device during storage, shipment and pre-use handling. In addition, the channel serves to cause/assist in coating the device with fluorinated liquids by substantially conforming to the shape of the device. The channel may also be treated in a manner that directs the flow of the fluorinated liquids, which by their nature are substantively omniphobic, resisting interactions with both aqueous (hydrophobic) and non-aqueous oily materials (oleophobic). The substantially conforming shape of the channel limits the amount of the fluorinated liquid that needs to be introduced into the channel to coat the desired surfaces of the medical device. All or part of the channel can be selectively treated to make it wettable with the fluorinated liquid (e.g., having a contact angle less than 90, 80, 70, 60, 50, 40, 30, 20, or 10 degrees with perfluoro decalin at 22° C.) and/or make it hydrophilic such that it repels the fluorinated liquid.

A. Packaging System Bases

The bases of the packaging systems described herein may, in some embodiments, be prepared from a solid block of material that may be formed by casting, additive manufacturing or other means. The channel for holding the medical device in the block of material may be formed during casting or additive manufacturing, or by milling the channel into the block. In other embodiments, the base may be formed either completely or substantially from a sheet of material that is stamped, pressed, or formed by injection molding. In some embodiments, when formed from or as a sheet of material, the base may have a substantially uniform thickness (less than 20%, 10% or 5% variation in thickness from the thickest point to the thinnest point). In other embodiments, when formed from a sheet of material, or formed as a sheet of material, it may not have a uniform thickness, varying by greater than 20%, 30% or 40% (e.g., from about 20% to about 50%) from the thinnest to the thickest point.

Regardless of whether the base of the packaging system is formed from a block or sheet of material, the base should substantially retain its shape when the medical device and fluorinated liquid (e.g., fluorinated hydrocarbon or perfluorinated hydrocarbon such as perfluorodecalin) are placed in the base. In an embodiment, the base is prepared from a material that is flexible, but retains its shape under the weight of the medical device and fluorinated liquid so as to retain and/or control the flow of the fluorinated liquid.

The base of the packaging system may be made of any suitable material including, but not limited to, metal, ceramic, glass (e.g., fiberglass), polymer/plastic (e.g., thermoset or thermoplastic) or combinations of any of the foregoing. In an embodiment, the base is prepared from a polymeric and/or plastic material. In some embodiments where the base is prepared from a polymer and/or plastic material, the material may be selected from the group consisting of low density polyethylene, high density polyethylene, polypropylene, polyethylene terephthalate, polyvinyl chloride, fluoropolymer, perfluoropolymer and combinations thereof.

The base and the channel within the base may be subject to a variety of treatments that render all or part of the base and/or all or part of the channel hydrophilic (e.g., ozonolysis or oxygen plasma treatment), hydrophobic or omniphobic. By rendering part of the base omniphobic by chemical treatment (e.g., by treatment with a fluoroalkyl silanizing agent such as 1H,1H,2H,2H-perfluorooctyl-trichlorosilane) or by the incorporation of a fluoroalkyl or perfluoroalkyl polymer into the base, the flow of fluorinated liquids may be controlled in the packaging system as the fluorinated liquids bind to and interact with otherwise omniphobic surfaces. In an embodiment, a strip along the base of the channel is made omniphobic and wettable with the fluorinated liquid (e.g., having a contact angle less than 90, 80, 70, 60, 50, 40, 30, 20, or 10 degrees with perfluorodecalin at 22° C.) by incorporating a fluoropolymer or perfluoropolymer strip along the base of the channel or by chemically treating a strip along the base of the channel, with at least a portion of the remainder of the channel either untreated or rendered hydrophilic (e.g., having a contact angle less than 90, 80, 70, 60, 50, 40, 30, 20, or 10 degrees with water at 22° C.).

B. The Channel System

The channel of the packaging system may be contained completely within one face of the base or may extend to the edge of the base where it can be exposed and accessed by removing (peeling away) or cutting away all or part of the cover. The surface of the base in which the channel is located may be substantially planar. The channel may be any shape (e.g., sinusoidal, zig-zag, etc.) and is not limited to the spiral configuration shown in FIG. 1.

In an embodiment, the channel is located in a substantially planar surface of the base, and the channel is disposed wholly or partly in the substantially planar surface. In another embodiment, the base has a substantially planar surface and one or more sides 8 abutting the substantially planar surface; and the channel 2 is formed in the substantially planar surface and does not extend to any of the one or more sides and is not exposed (or accessible by removal of the cover on any of the one or more sides). In another embodiment, the base has a substantially planar surface and one or more sides 8 abutting the substantially planar surface, and the channel 2 is formed in the substantially planar surface and extends to at least one of the one or more sides 8 and forms an exposed and/or accessible end 9 of the channel on at least one of the one or more sides of the base (e.g., by removing or peeling the cover away such as with tab 5). In such an embodiment, the medical device, or a connector to the medical device, may be accessible from the side of the packaging system once the cover is removed from the side of the base. The connector may be used to handle/ grasp the medical device. When the connector is in fluid communication with an interior space of the medical device (e.g., an inner lumen of a device having a tubular portion), it may be used to introduce the fluorinated liquid into an interior space of the medical device and the channel if the interior space opens into the channel (e.g., at its distal end). See e.g., the embodiment shown in FIG. 1.

In an embodiment, the channel may have a region which may be constricted 10 and which engages either the medical device or a connector to the medical device, firmly holding it in position. The constricted region may be located to engage a portion near one end of an elongated medical device.

As discussed above, portions of the channel may be made from materials that are wettable with the fluorinated liquid (e.g., fluoropolymers or perfluoropolymers), or may be treated with material that renders a portion of the channel wettable with the fluorinated liquid.

Any or all of the optional expanded region, the region adjacent to the side (e.g., constricted region), or the exposed end of the channel 9 may be hydrophilic such that the fluorinated liquid will be repelled from any of those regions and retained in the channel.

The channel of the medical device packaging system described herein substantially conforms to the medical device that will be packaged in the packaging system. In an embodiment, the volume of the channel unoccupied by the medical device, the unoccupied volume including the volume of any interior spaces of the medical device accessible to a fluorinated liquid, is less than 10, 25, 30, 40, 50, 60, 70, 80, 90, 100, 125, 150, 200, 250, 300 or 400 percent of the volume of the medical device. In another embodiment the volume of the channel unoccupied by the medical device, the unoccupied volume including the volume of any interior spaces of the medical device accessible to a fluorinated liquid, is in a range selected from 10-25, 25-50, 50-75, 75-100, 100-150, 150-200, 200-250, 250-300 or 300-400 percent of the volume of the medical device. In another embodiment, the channel has a volume less than 400%, 300%, 250%, 200%, 175%, 150%, 125% or 110% of the volume of the medical device that is accessible to the fluorinated liquid.

C. Packaging System Covers

In order to maintain the sterility of the channel and any medical device disposed therein, the packaging system employs a cover that forms a substantially gas and liquid tight seal over the channel. The cover may be attached or affixed to the base by any means known in the art including, but not limited to, heat sealing the cover to the base (e.g., where the base and cover are made from thermoplastic), ultra-sonic welding, adhesives, and/or pressure sensitive glue for peel-away (semi-permanent) covers. In an embodiment, the channel is formed in a substantially planar surface of the base and the cover is affixed to the substantially planar surface. In an embodiment where the channel is formed in the upper surface of the base and is accessible from the side of the base, the cover may extend over all or part of the side (e.g., as a tab) of the base to seal the channel. In such an embodiment, all or part of the cover may be separated from the base, exposing the end of the channel and the medical device or a portion of the connector. Once exposed the fluorinated liquid may be introduced into the medical device or the channel via the exposed end.

Material choices for the base and cover will be dictated in large part based upon the type of sterilization process to be employed. For example, plastics will generally be used where the sterilization process is radiation or ethylene oxide based. While it is possible to use radiation, where the packaging or medical device contains fluorinated polymers or liquids, care must be taken to limit the dose so as not to cause release of HF, whose production should be closely monitored. Where ethylene oxide or another gaseous material is selected as the sterilizing agent, the lid and/or base is selected to be permeable to ethylene oxide or the gaseous material. Ethylene oxide permeable materials include polymeric materials including, but not limited to, low density polyethylene. To increase the permeability of the films to ethylene oxide, the films may be made from membranes or sheet(s) having a thickness of less than 500 microns, 400 microns, 300 microns, 200 microns, 100 microns, 75 microns, 50 microns, or 25 microns. For added strength the films may be reinforced with, or backed with, woven or non-woven fibers.

In some embodiments the cover and/or the base of the packaging system is opaque or non-transparent. In other embodiments, the cover and/or base of the packaging system is translucent and/or clear.

D. The Packaged Devices

The medical devices disposed in the channel of the packaging systems generally will have one or more surfaces, or components with at least one surface, that will wet with one or more fluorinated and/or perfluorinated liquids. Surfaces of the medical devices that interact with the liquids will generally be formed from one or more fluoropolymers and/or perfluoropolymers. The surfaces may also be chemically treated to incorporate fluoroalkyl groups that can interact with the fluorinated liquids.

In an embodiment, the medical device comprises a component comprised of one or more fluoropolymers and/or perfluoropolymers, or a coating on all or part of the medical device or a component of the medical device is comprised of a fluoropolymer and/or perfluoropolymer.

In an embodiment, the medical device comprises a tubular structure having an inner lumen and/or an internal space. In one such embodiment, the packing system includes a connector attached to the medical device. The connector may be in fluid communication with the inner lumen and/or the internal space of the medical device. The medical device and/or connector may include one or more fittings permitting fluid tight connection to be made to the medical device. Such fittings may be one or more luer lock fittings. The connector may, for example, have two luer fittings (e.g., a male and a female luer fitting, two female luer fittings, or two male luer fittings), one of which is attached to the medical device and the other of which provides a location for attachment of a reservoir of fluorinated liquid that can be introduced into the medical device and/or channel. In an embodiment, the connector comprises a sterile filter having a pore size less than 0.4 microns, 0.2 microns or 0.1 microns. In such an embodiment, the sterile filter may be made from materials that are stable (do not swell, leak or change dimensions or pore size) in perfluorodecalin for greater than 5, 10, 15 or 30 minutes at 22° C.

In an embodiment, the medical device or one or more components of the medical device comprises one or more fluoropolymers and/or perfluoropolymers. In such an embodiment, the one or more fluoropolymers and/or perfluoropolymers may be selected independently from the group consisting of perfluoroalkoxy alkanes (PFA or PFAs when plural); polytetrafluoroethylene (PTFE); fluorinated ethylene propylene (FEP); expanded polytetrafluoroethylene (ePTFE or EPTFE); expanded fluorinated ethylene propylene (eFEP or EFEP); perfluoromethylvinylether (PMVE); perfluoro elastomers (e.g., FFKM, which are copolymers of tetrafluoroethylene and a perfluorinated ether such as PMVE sold under the tradenames TECNOFLON®, TECNOFLON® PFR, branded as KALREZ®, CHEMRAZ® and PERLAST®) and combinations thereof. The fluoropolymers that may be employed include, but are not limited to, ethylene tetrafluoroethylene (ETFE); polyvinylidene fluoride (PVDF); fluoroelastomers: (FKM and FEPM sold under the tradenames VITON®, TECNOFLON®); vinylidene fluoride-hexafluoropropylene fluoroelastomer (VF2/HFP); vinylidene fluoride-hexafluoropropylene/tetrafluoro ethylene/hexafluoropropylene fluoroelastomer (VF2/tetrafluoro ethylene/HFP) terpolymer; and combinations thereof.

Examples of medical devices that may be packaged in the systems described herein include, but are not limited to, catheters, shunts, stents, pumps, valves, tubing, grafts, artificial organs (lungs, heart, joints), and surgical instruments, all or any portion of which may be comprised of a fluoropolymer or a perfluopolymer.

E. The Fluorinated Liquid

As noted above the fluorinated liquids used herein are liquid at 22° C. and one atmosphere of pressure and are comprised of, consist essentially of, or consist of hydrocarbons, or molecules having a hydrocarbon moiety (e.g., an alkyl group) in which one or more hydrogen atoms bound to a carbon atom have been replaced by a fluorine atom, and the perfluorocarbons have each hydrogen atom replaced by a fluorine atom. Although the term fluorinated liquid encompasses perfluorinated liquids, the term fluorinated and/or perfluorinated liquids is used to emphasize that mixtures of fluorinated and perfluorinated liquids may be employed.

A variety of fluorinated liquids and/or perfluorinated liquids may be employed in the packaging systems described herein. In an embodiment, the fluorinated liquid is comprised of, comprised essentially of, or consists of one or more fluorinated hydrocarbons and/or perfluorinated hydrocarbons, and/or one or more molecules with fluoroalkyl groups or perfluoroalkyl groups. In an embodiment, the fluorinated liquid comprises a perfluorinated hydrocarbon. In an embodiment, the fluorinated liquid comprises a fluorinated alkane. In an embodiment, the fluorinated liquid comprises a perfluorinated alkane. In an embodiment the fluorinated liquid includes, but is not limited to, one or more solvents selected from: perfluoropropane, perfluorobutane, perfluoropentane, perfluorohexane, perfluorooctane, perfluorodecalin, perfluoroperhydrophenanthrene, perfluorooctylbromide, perfluoro tributyl amine, perfluorotripentyl amine, poly(hexafluoropropylene oxide) and combinations thereof. In an embodiment, the fluorinated liquid comprises perfluoro tributyl amine. In one embodiment, the fluorinated liquid comprises perfluorodecalin.

In an embodiment, the packaging system comprises one or more fluorinated liquids.

F. Reservoirs for Holding Fluorinated Liquids and the Introduction of Fluorinated Liquids into the Channel Application of the fluorinated liquids to the medical devices disposed in the channel may be conducted during manufacturing and, if necessary, supplemented at the time of use when an aliquot of fluorinated liquid is added. Alternatively, the fluorinated liquid may be packaged in a reservoir and added to the channel and medical device therein just prior to the time of use.

Any of a variety of vessels or containers may serve as a reservoir for the fluorinated liquids. Vessels or containers that may be employed to contain the fluorinated liquid include, but are not limited to, syringes, flexible bags or pouches, canisters, or any other reservoir which will (a) safely hold the liquid for an extended period of time, and (b) allow the liquid to be applied to the packaged device without compromising the device sterility. The reservoir will have to be resistant to or impervious to the fluorinated liquids. In some embodiments reservoirs will be sterilized either prior to being filled with sterile aliquots of the liquid or sterilized with aliquots of the fluorinated liquid contained therein, provided the fluorinated liquid is not degraded or lost by the sterilization. Alternatively, the fluorinated liquid may be subject to sterilization by filtration at the time of application to the medical device (e.g., through a filter serving as a connector) and/or to the packaging (e.g., addition to the channel) containing the medical device.

In an embodiment the base and/or cover of the packaging system are stable to perfluorodecalin for 5, 10, 15, 20, 25 or 30 minutes at 22° C.

In an embodiment, the fluorinated liquid is contained in a reservoir separately from the channel. In such an embodiment the reservoir may be comprised of one or more polymers, ceramics, glasses, metals, silicones and/or combinations thereof. Examples of reservoirs include, but are not limited to, syringes, bottles, or flexible bags/pouches.

Figure 2A:
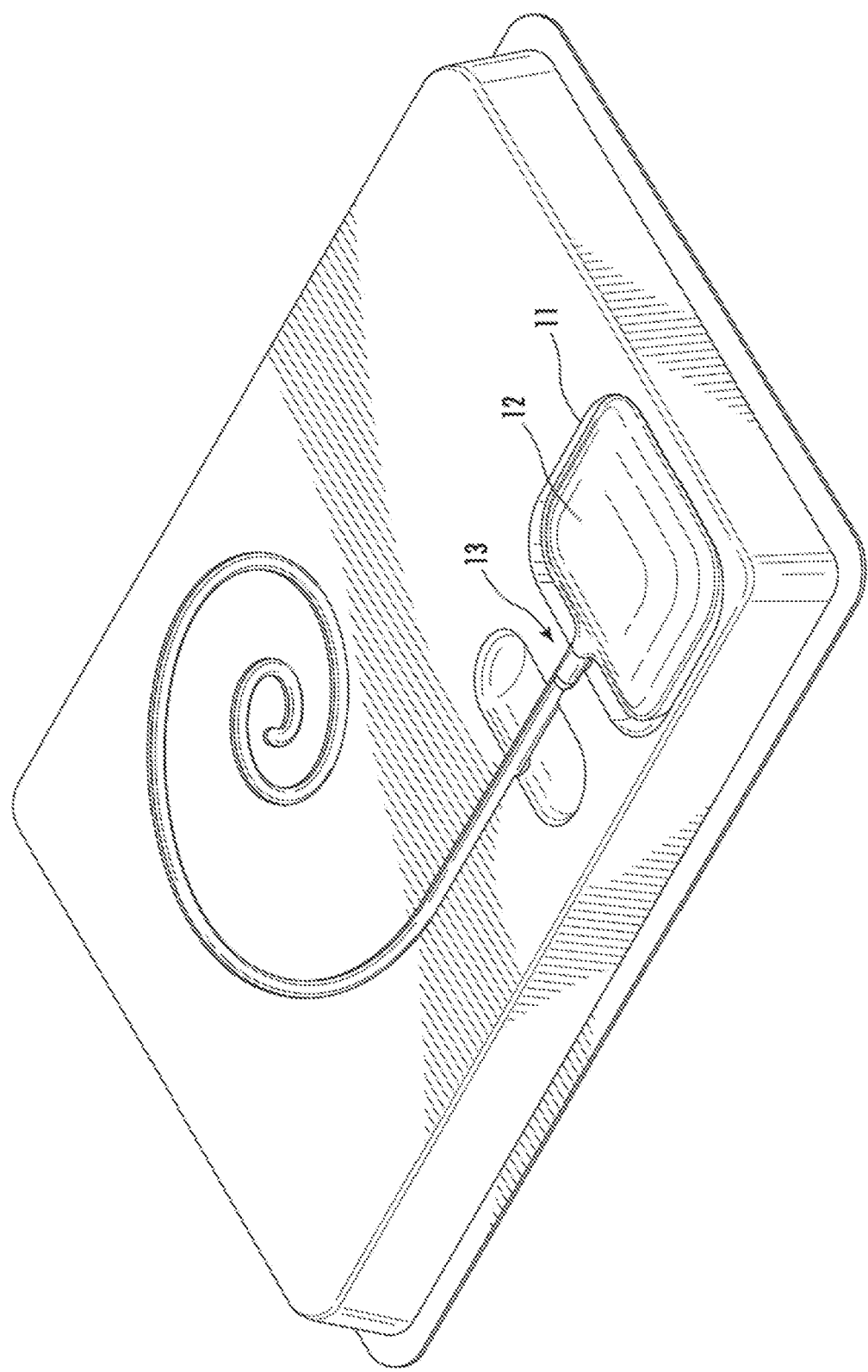
FIG. 2A shows an embodiment of a medical device packaging system as described in FIG. 1; however the channel does not extend to the side of the base and instead terminates in a depression 11 in the base in which a reservoir 12 (e.g., a compressible pouch) filled with a fluorinated liquid is attached to and in fluid communication with a medical device in the channel via a tube containing a one-way valve, breakable membrane, or the like 13, which may additionally contain a sterile filter (not shown).
Figure 2B:
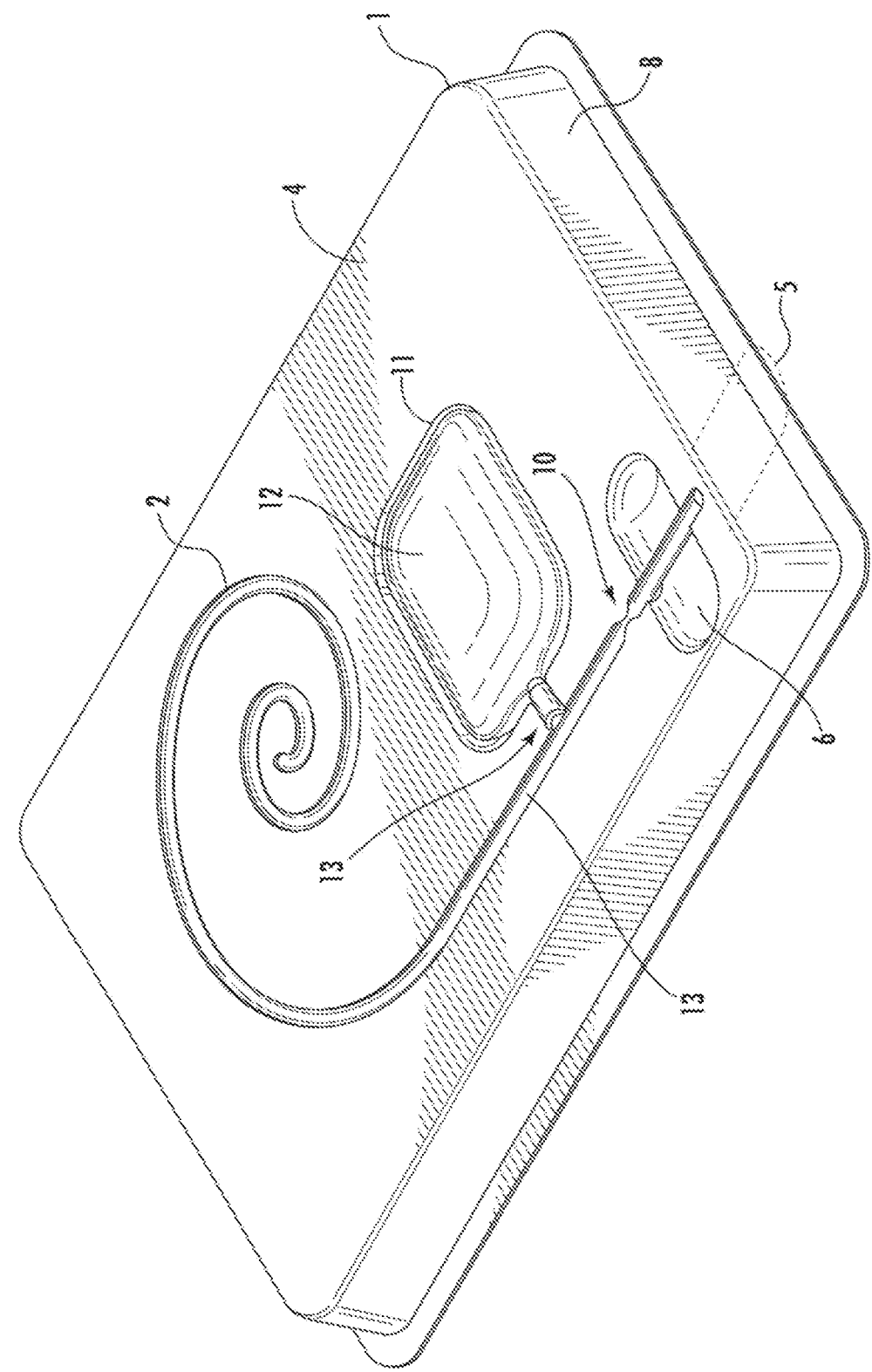
FIG. 2B shows a medical device packaging system as in FIG. 2A; however, the depression 11 containing the reservoir 12 is connected to the channel via a side channel/tube containing a one-way valve, breakable membrane, or the like 13.

In one embodiment, the base of the packaging system comprises a depression 11 for holding the reservoir 12 loaded with fluorinated liquid. In one such embodiment, the reservoir and the channel are in inducible fluid communication connected by a valve or breakable membrane 13; wherein fluid in the reservoir may be induced to move into the channel by i) providing sufficient pressure (force) on the liquid and opening the valve between the reservoir and the channel to cause the fluorinated liquid to move into the channel, or ii) providing sufficient force on the liquid to break the membrane to cause the fluorinated liquid to move into the channel. See, e.g., FIG. 2B. The medical device and channel as well as the fluorinated liquid in the reservoir may all be sterile prior to the addition of the fluorinated liquid to the channel and device.

II. Methods of Packaging a Medical Device

The present disclosure describes and includes methods for packaging medical devices that are to be coated, treated, or lubricated with a fluorinated (e.g., perfluorinated liquid) as a means of preventing thrombus formation, cell adhesion, and/or biofilm adhesion/growth. The methods may include placing the medical device, or a component of a medical device, in a confined region or channel formed in the base of a packaging system. The methods may further include enclosing the medical device in the channel with a cover that forms a substantially gas and liquid tight seal over the channel. The cover maintains the sterility of materials in the channel and may be permeable to a sterilizing agent such as ethylene oxide. The perfluorinated liquid can be applied to the device in the channel at the time the device is packaged, or the liquid can be added to the device at the point of care.

In an embodiment, a reservoir containing fluorinated liquid may also be packaged with the medical device. For convenience, the reservoir may be held in a depression in the base of the package alongside of the channel housing the medical device and may be located under the cover.

In an embodiment, the reservoir containing fluorinated liquid (e.g., a flexible bag or pouch) is packaged in a depression 11 in the base of the package alongside of the channel 2 housing the medical device 3. The channel and the depression holding the reservoir are joined by a tube or channel through which fluorinated liquid held in the reservoir may be forced into the medical device (see, e.g., FIG. 2A) or the channel with the medical device (see, e.g., FIG. 2B) through a tube containing a one-way valve, breakable membrane 13 or the like by applying pressure to the fluorinated liquid.

III. Methods of Treating a Medical Device with a Fluorinated Liquid

The present disclosure includes and provides for methods of treating a medical device with one or more fluorinated liquids.

In an embodiment, one or more fluorinated liquids are applied to the medical device disposed in the channel at the time of manufacture and the packaged device subjected to sterilization with, for example, radiation or ethylene oxide (provided the cover and/or base are permeable to ethylene oxide).

In some embodiments, one or more fluorinated liquids are applied to the medical device after manufacturing, typically at the point of care. In such instances, the one or more fluorinated liquids, which are held in a reservoir (e.g., a sealed vessel or container), may be applied to the device by introducing the liquid into the channel by one or more various methods (e.g., removing part of the cover and adding the fluorinated liquids). One such method includes introducing the liquid into the channel around the device by injecting the fluorinated liquids (e.g., with a needle and syringe through the cover or base (e.g., directly or through a septum in the cover or base) and permitting it to coat the device. Another such method includes introducing the fluorinated liquid into the channel through the device itself (e.g., flowing liquid into a catheter packaged in the channel and allowing it to flow out the distal end of the catheter into the channel and around the device). The channels can be designed to encourage the liquid to flow in a manner such that it contacts all, or substantially all (e.g., greater than 80%, 85%, 90%, or 95%) of the liquid accessible surface area of the medical device. One means by which the channel can be designed to encourage fluorinated liquids to contact the desired portions of the device is by having the channel conform to the shape of the device and/or by introduction of the fluorinated liquid into the channel through one or more application points. Another means by which the channel can be designed to encourage fluorinated liquids to contact the desired portions of the device is, as discussed above, by providing regions that are hydrophobic or that interact with (e.g., become wetted by) the fluorinated liquids. Once all, or the desired portion, of the medical device is coated with the fluorinated liquids, the device can be removed from the packaging and used for its medical purpose.

In an embodiment, the fluorinated liquids are introduced into the channel or into the medical device by exposing an end of the medical device and/or a connector attached to the medical device and in liquid communication with the medical device (e.g., at the side of the base) and introducing the fluorinated liquid into the channel or medical device.

In an embodiment, the packaging system comprises a reservoir and the channel in inducible fluid communication connected by a valve or breakable membrane, and the fluid in the reservoir is induced to move into the channel by i) providing sufficient pressure (force) on the liquid and opening the valve between the reservoir and the channel to cause the fluorinated liquid to move into the channel, or ii) providing sufficient force on the liquid to break the membrane to cause the fluorinated liquid to move into the channel.

In an embodiment, the medical device comprises a tubular structure having an inner lumen and/or an internal space having an inlet and an outlet and a connector (e.g., a sterile filter or length of tubing). The connector is in fluid communication with the inlet of the inner lumen and/or the internal space of the medical device and the fluorinated liquid is introduced into the channel by exposing an end of the connector attached to the medical device and introducing the fluorinated liquid (e.g., from a reservoir) into the connector, thereby introducing the fluorinated liquid into the lumen and/or internal space of the medical device. After flowing through all or part of the medical device, the fluorinated liquid flows into the channel through the outlet, thereby contacting the outer surface of the medical device. In such an embodiment the outlet may be located at or in a portion of the medical device distal to the inlet.

In an embodiment, sufficient fluorinated liquid is introduced to fill the lumen or internal space of the medical device and cause at least a portion of the liquid into the channel surrounding the medical device. In one method of treating a medical device with fluorinated liquids, after the fluorinated liquid is introduced into the medical device a bolus of a gas (e.g., air) is introduced into the device to force at least a portion of the fluorinated liquid out of the medical device and into the channel through any outlets in the medical device.

In an embodiment, the method comprises introducing sufficient fluorinated liquid into the channel to fill greater than 50%, 60%, 70%, 80%, 90%, or 100%, (e.g., 50%-60%, 60%-70%, 70%-80%, 80%-90% or 90%-100%) of the volume of the channel. In an embodiment, the method comprises introducing sufficient fluorinated liquid into the channel to fill greater than 50, 60, 70, 80, 90, or 100%, of the volume of the channel not occupied by the medical device, wherein the volume of the channel not occupied by the medical device includes the volume of any interior spaces of the medical device accessible to the fluorinated liquid. In some instances, when the fluorinated fluid is introduced, the base is inclined such that introduction of the fluorinated fluid occurs at a location that is elevated relative to at least a portion of the channel.

Certain Embodiments

1. A medical device packaging system comprising:
   (i) a base having a channel substantially conforming to the shape of a medical device, wherein the channel has a volume;
   (ii) a cover forming a substantially gas and liquid tight seal over the channel (thereby closing the channel from the external environment), wherein the cover can be peeled away from the base exposing all or part of the channel (can be slit, perforated with a knife if desired); and
   (iii) a medical device disposed in the channel, (the medical device optionally comprising fluoropolymer and/or perfluoropolymer component(s) or coating on all or part of its surface);
   wherein the medical device optionally comprises a connector to the medical device that is also disposed in the channel.

2. The packaging system of embodiment 1, wherein the medical device comprises a fluoropolymer and/or perfluoropolymer.
3. The packaging system of embodiment 2, wherein the medical device comprises a component comprised of a fluoropolymer and/or perfluoropolymer, or a coating on all or part of a component comprised of a fluoropolymer and/or perfluoropolymer.
4. The packaging system of any preceding embodiment wherein the base is formed of a solid block of material.
5. The packaging system of any of embodiments 1 to 3, wherein the base is made of a formed sheet of material.
6. The packaging system of embodiment 5, wherein the sheet is not of uniform thickness.
7. The packaging system of embodiment 5, wherein the sheet is of uniform thickness.
8. The packaging system of any of embodiments 5 to 7, wherein the base is flexible but substantially retains its shape under the weight of the medical device.
9. The packaging system of any preceding embodiment, wherein the base is made by additive manufacturing, casting, injection molding, stamping, or pressing.
10. The packaging system of any preceding embodiment, wherein the base is made from polymeric material.
11. The packaging system of embodiment 10, wherein the polymeric material is selected from the group consisting of: low density polyethylene, high density polyethylene, polypropylene, polyethylene terephthalate, polyvinyl chloride fluoropolymers, perfluoropolymers, and combinations thereof.
12. The packaging system of any preceding embodiment, wherein the volume of the channel unoccupied by the medical device, the unoccupied volume including the volume of any interior spaces of the medical device accessible to a fluorinated liquid, is less than 10, 25, 50, 60, 70, 80, 90, 100, 125, 150, 200, 250, or 300% of the volume of the medical device.
13. The packaging system of any preceding embodiment, wherein the volume of the channel unoccupied by the medical device, the unoccupied volume including the volume of any interior spaces of the medical device accessible to a fluorinated liquid, is in a range selected from 10-25, 25-50, 50-75, 75-100, 100-150, 150-200, 200-250 or 250-300% of the volume of the medical device.
14. The packaging system of any of embodiments 1 to 11, wherein the channel has a volume less than 300%, 250%, 200%, 175%, 150%, 125% or 110% of the volume of the medical device.
15. The packaging system of any preceding embodiment, wherein the base has a substantially planar surface, and the channel is disposed wholly or partly in the substantially planar surface.
16. The packaging system of any preceding embodiment, wherein the base has a substantially planar surface and one or more sides abutting the substantially planar surface; and
    wherein the channel is formed in the substantially planar surface and does not extend to any of the one or more sides and is not exposed on any of the one or more sides.
17. The packaging system of any of embodiments 1 to 15, wherein the base has a substantially planar surface and one or more sides abutting the substantially planar surface; and
    wherein the channel is formed in the substantially planar surface and extends to at least one of the one or more sides and is exposed and/or accessible on at least one of the one or more sides of the base (where the channel extends to the side).
18. The packaging system of embodiment 17, wherein at least an end of the medical device disposed in the channel, or the connector to the medical device disposed in the channel, is exposed and/or accessible on at least one side of the one or more sides of the base (where the channel extends to the side).
19. The packaging system of any preceding embodiment, wherein the channel includes an expanded area permitting access to the medical device by human fingers and/or forceps.
20. The packaging system of embodiment 17 or 18, wherein the portion of the channel proximal to the point at which the channel is exposed to at least one of the one or more sides comprises a constriction that engages the medical device or the connector to the medical device.
21. The packaging system of any preceding embodiment wherein the medical device comprises a tubular structure having an inner lumen and/or an internal space.
22. The packaging system of embodiment 21, wherein the connector to the medical device is in fluid communication with the inner lumen and/or the internal space of the medical device.
23. The packaging system of embodiment 22, wherein the connector comprises one or more luer fittings (e.g., a male and a female luer fitting, two female luer fittings, and two male luer fittings).
24. The packaging system of any of embodiment 22 or 23, wherein the connector is a sterile filter with a pore size less than 0.4 microns, 0.2 microns or 0.1 microns.
25. The packaging system of embodiment 24, wherein the filters are stable in perfluorodecalin for greater than 5 minutes.
26. The packaging system of any preceding embodiment wherein the cover is in the form of a sheet or film with a thickness less than 500 microns, 400 microns, 300 microns, 200 microns, 100 microns, 75 microns, 50 microns, or 25 microns.
27. The packaging system of any preceding embodiment, wherein all or part of the cover is affixed to the base in a semi-permanent manner (glue, contact adhesive, etc.), and may be separated in whole or in part from the base (e.g., peel away).
28. The packaging system of any of embodiments 16 to 27, wherein the cover is affixed to the substantially planar surface.
29. The packaging system of embodiment 28 wherein the cover is also affixed to at least one side of the base.
30. The packaging system of any of embodiments 17 to 27, wherein the cover is affixed to the substantially planar surface and forms a substantially gas and liquid tight seal over the part of the channel formed in the substantially planar surface and the portion of the channel exposed or accessible on the one or more sides of the base; and wherein the cover optionally has a tab along or at an edge to assist in its separation from the base.
31. The packaging system of embodiment 30, wherein the cover may be removed from a side of the base (e.g., peeled back) to expose a portion of the channel, the medical device, and/or a connector attached to the medical device.

32. The packaging system of any preceding embodiment, wherein the cover has one or more tabs not affixed to the base (for grasping the edge of the cover and removing it).
33. The packaging system of any of embodiments 30 to 32, wherein the tab is attached to the cover proximal to the portion of the channel exposed or accessible on the one or more sides of the base.
34. The packaging system of any preceding embodiment, wherein all or part of the cover is permeable to ethylene oxide and permits ethylene oxide to reach the medical device.
35. The packaging system of any preceding embodiment, wherein the cover is opaque.
36. The packaging system of any preceding embodiment, wherein the cover is translucent or clear.
37. The packaging system of any preceding embodiment, wherein the cover is comprised of a polymeric material.
38. The packaging system of embodiment 37, wherein the cover comprises low density polyethylene.
39. The packaging system of any preceding embodiment, wherein the cover further comprises woven or non-woven fibers.
40. The packaging system of any preceding embodiment, wherein the fluoropolymers and/or perfluoropolymers are selected from the group consisting of: perfluoroalkoxy alkanes (PFA or PFAs when plural); polytetrafluoroethylene (PTFE); fluorinated ethylene propylene (FEP); expanded polytetrafluoroethylene (ePTFE or EPTFE); expanded fluorinated ethylene propylene (eFEP or EFEP); perfluoromethylvinylether (PMVE); perfluoro elastomers (e.g., FFKM, which are copolymers of tetrafluoroethylene and a perfluorinated ether such as PMVE sold under the tradenames TECNOFLON®, TECNOFLON® PFR, branded as KALREZ®, CHEMRAZ® and PERLAST®); ethylene tetrafluoroethylene (ETFE); polyvinylidene fluoride (PVDF); fluoroelastomers (FKM and FEPM sold under the tradenames VITON®, TECNOFLON®); vinylidene fluoride-hexafluoropropylene fluoroelastomer (VF2/HFP); vinylidene fluoride-hexafluoropropylene/tetrafluoro ethylene/hexafluoropropylene fluoroelastomer (VF2/tetrafluoro ethylene/HFP) terpolymer; and combinations thereof.
41. The packaging system of any preceding embodiment, further comprising a fluorinated liquid.
42. The packaging system of embodiment 41, wherein the fluorinated liquid comprises or is one or more perfluorinated liquids.
43. The packaging system of embodiment 41, wherein the fluorinated liquid is a fluorinated alkane or a perfluorinated alkane.
44. The packaging system of embodiment 41, wherein the fluorinated liquid includes, but is not limited to, one or more solvents selected from: perfluoropropane, perfluorobutane, perfluoropentane, perfluorohexane, perfluorooctane, perfluorodecalin, perfluoroperhydrophenanthrene, perfluorooctylbromide, perfluoro tributyl amine, perfluorotripentyl amine, poly(hexafluoropropylene oxide) and combinations thereof.
45. The packaging system of any of embodiments 41 to 44, wherein the base is stable to the fluorinated liquid for at least 5 minutes at 22° C.
46. The packaging system of any preceding embodiment, wherein the cover is stable to the fluorinated liquid for at least 5 minutes at 22° C.
47. The packaging system of any of embodiments 41 to 46, wherein the fluorinated liquid is contained in a reservoir separately from the channel.
48. The packaging system of embodiment 47, wherein the fluorinated liquid is contained in a syringe, bottle, or flexible bag/pouch.
49. The packaging system of embodiment 47 or 48, wherein the reservoir is comprised of a polymer, ceramic, glass, metal, silicone or combinations thereof (or another material which imperviously holds the liquid).
50. The packaging system of any of embodiments 41 to 45, comprising fluorinated liquid in the channel.
51. The packaging system of any preceding embodiment wherein the base further comprises a depression for holding a reservoir, the reservoir containing a fluorinated liquid located therein.
52. The packaging system of embodiment 51 wherein the reservoir and the channel are in inducible fluid communication connected by a valve or breakable membrane; wherein fluid in the reservoir may be induced to move into the channel by i) providing sufficient pressure (force) on the liquid and opening the valve between the reservoir and the channel to cause the fluorinated liquid to move into the channel, or ii) providing sufficient force on the liquid to break the membrane to cause the fluorinated liquid to move into the channel.
53. The packaging system of any of embodiments 47 to 52, wherein the channel and the medical device disposed therein are sterile.
54. The packaging system of any of embodiments 41 to 53, wherein the fluorinated liquid in the reservoir is sterile.
55. A method for treating a medical device with a fluorinated liquid comprising obtaining a medical device packaging system according to any preceding embodiment and introducing the fluorinated liquid into the channel, wherein the channel has a volume.
56. The method according to embodiment 55, wherein the fluorinated liquid is introduced into the channel by injection (e.g., with a needle and syringe) into the channel through the cover, the base, or a septum provided in either the cover or base.
57. The method according to embodiment 55, wherein the fluorinated liquid is introduced into the channel or to the medical device by: removing all or part of the cover to expose an end of the medical device and/or all or part of the channel; and delivering the fluorinated liquid to the exposed end of the medical device and/or an exposed part of the channel.
58. The method according to embodiment 55, wherein the fluorinated liquid is introduced into the channel or to the medical device by exposing an end of the medical device and/or a connector attached to the medical device and in liquid communication with the medical device followed by introducing the fluorinated liquid to the exposed end of the medical device and/or the exposed end of the connector.
59. The method according to embodiment 55, wherein the packaging system comprises a reservoir and the channel in inducible fluid communication connected by a valve or breakable membrane, and the fluid in the reservoir is induced to move into the channel by i) providing sufficient pressure (force) on the liquid and opening the valve between the reservoir and the channel to cause the fluorinated liquid to move into the channel, or ii) providing sufficient force on the liquid to break the membrane to cause the fluorinated liquid to move into the channel.

60. The method according to embodiment 55, wherein the medical device comprises a tubular structure having an inner lumen and/or an internal space having an inlet and an outlet;

wherein when a connector is present the connector is in fluid communication with the inlet of the inner lumen and/or the internal space of the medical device; and wherein the fluorinated liquid is introduced into the channel by exposing an end of the medical device and/or the connector attached to the medical device and introducing the fluorinated liquid into the medical device or the connector, thereby introducing the fluorinated liquid into the lumen and/or internal space of the medical device and the channel as liquid exits the medical device through the outlet.

61. The method according to embodiment 60, wherein the outlet is located at or in a portion of the medical device distal to the inlet.

62. The method of embodiment 60 or 61, wherein sufficient fluorinated liquid is introduced to fill the lumen or internal space of the medical device and cause at least a portion of the liquid to flow into the channel.

63. The method of any of embodiments 60 to 62, wherein the fluorinated liquid is introduced into the medical device followed by a bolus of a gas (e.g., air) to force at least a portion of the fluorinated liquid out of the medical device and into the channel.

64. The method of any of embodiments 55 to 63, wherein sufficient fluorinated liquid is introduced into the channel to fill greater than 10%, 20%, 30%, 40%, 50%, 60%, 70%, 80%, 90%, or 100% (e.g., 10%-20%, 20%-30%, 30%-40%, 40%-50%, 50%-60%, 60%-70%, 70%-80%, 80%-90% or 90%-100%) of the volume of the channel.

65. The method of any of embodiments 55 to 63, wherein sufficient fluorinated liquid is introduced into the channel to fill greater than 50%, 60%, 70%, 80%, 90% or 100% of the volume of the channel not occupied by the medical device, wherein the volume of the channel not occupied by the medical device includes the volume of any interior spaces of the medical device accessible to the fluorinated liquid.

66. The method of any of embodiments 55 to 65, wherein, when the fluorinated fluid is introduced, the base is inclined such that introduction of the fluorinated fluid occurs at a location that is elevated relative to at least a portion of the channel.

67. The method of any of embodiments 55 to 66, further comprising removing the device from the channel.

The invention claimed is:

1. A medical device packaging system comprising:
(i) a base having a channel substantially conforming to the shape of a medical device, the channel having a volume;
(ii) a cover forming a substantially gas and liquid tight seal over the channel, wherein the cover can be peeled away from the base exposing all or part of the channel; and
(iii) a medical device disposed in the channel, the medical device comprising a fluoropolymer and/or perfluoropolymer component or coating on all or part of its surface;
wherein the medical device comprises a connector to the medical device that is also disposed in the channel;
wherein the medical device comprises a fluoropolymer and/or perfluoropolymer; and
wherein the medical device further comprises a fluorinated liquid which comprises or is one or more perfluorinated liquids.

2. The packaging system of claim 1, wherein the base is made by additive manufacturing, casting, injection molding, stamping, or pressing.

3. The packaging system of claim 1, wherein the base is made from polymeric material.

4. The packaging system of claim 3, wherein the polymeric material is selected from the group consisting of: low density polyethylene, high density polyethylene, polypropylene, polyethylene terephthalate, polyvinyl chloride fluoropolymers, perfluoropolymers, and combinations thereof.

5. The packaging system of claim 1, wherein the channel has a volume less than 300% of the volume of the medical device.

6. The packaging system of claim 1, wherein the base has a substantially planar surface and one or more sides abutting the substantially planar surface; and
wherein the channel is formed in the substantially planar surface and extends to at least one of the one or more sides and is exposed to and/or accessible on at least one of the one or more sides of the base; and
wherein at least an end of the medical device disposed in the channel, or the connector to the medical device disposed in the channel, is exposed to and/or accessible on at least one side of the one or more sides of the base.

7. The packaging system of any of claim 1, wherein the medical device comprises a tubular structure having an inner lumen and/or an internal space.

8. The packaging system of claim 7, wherein the connector to the medical device is in fluid communication with the inner lumen and/or the internal space of the medical device.

9. The packaging system of claim 8, wherein the connector comprises one or more luer fittings.

10. The packaging system of claim 6, wherein the cover is affixed to the substantially planar surface and forms a substantially gas and liquid tight seal over the part of the channel formed in the substantially planar surface and the portion of the channel exposed to or accessible on the one or more sides of the base; and wherein the cover has a tab along or at an edge to assist in its separation from the base.

11. The packaging system of claim 10, wherein the cover may be removed from a side of the base to expose a portion of the channel, the medical device, and/or a connector attached to the medical device.

12. The packaging system of claim 1, wherein all or part of the cover is permeable to ethylene oxide and permits ethylene oxide to reach the medical device.

13. The packaging system of claim 1, wherein the fluoropolymers and/or perfluoropolymers are selected from the group consisting of: perfluoroalkoxy alkanes; polytetrafluoroethylene; fluorinated ethylene propylene; expanded polytetrafluoroethylene; expanded fluorinated ethylene propylene; perfluoromethylvinylether; perfluoro elastomers; ethylene tetrafluoroethylene; polyvinylidene fluoride; fluoroelastomers; vinylidene fluoride-hexafluoropropylene fluoroelastomer; vinylidene fluoride-hexafluoropropylene/tetrafluoro ethylene/hexafluoropropylene fluoroelastomer terpolymer; and combinations thereof.

14. The packaging system of claim 1, wherein the fluorinated liquid is a fluorinated alkane or a perfluorinated alkane.

15. The packaging system of claim 1, wherein the fluorinated liquid includes one or more solvents selected from:

perfluoropropane, perfluorobutane, perfluoropentane, perfluorohexane, perfluorooctane, perfluorodecalin, perfluoroperhydrophenanthrene, perfluorooctylbromide, perfluoro tributyl amine, perfluorotripentyl amine, poly(hexafluoropropylene oxide) and combinations thereof.

16. The packaging system of claim 1, wherein the fluorinated liquid is contained in a reservoir separately from the channel.

17. The packaging system of claim 16, wherein the fluorinated liquid is contained in a syringe, bottle, or flexible bag/pouch.

18. The packaging system of claim 16, wherein the reservoir is comprised of a polymer, ceramic, glass, metal, silicone or combinations thereof.

19. The packaging system of claim 16, wherein the channel and the medical device disposed therein are sterile.

20. A method for treating a medical device with a fluorinated liquid comprising obtaining a medical device packaging system according to claim 1 and introducing the fluorinated liquid into the channel, wherein the channel has a volume.

* * * * *